United States Patent [19]

Meiattini

[11] 4,306,020
[45] Dec. 15, 1981

[54] COMPOSITION FOR THE ANALYSIS OF THE ALKALINE PHOSPHATASE AND METHOD THEREFOR

[75] Inventor: Franco Meiattini, Siena, Italy

[73] Assignee: Istituto Sieroterapico E Vaccinogeno Toscano "SCLAVO" S.p.A., Siena, Italy

[21] Appl. No.: 190,794

[22] Filed: Sep. 25, 1980

Related U.S. Application Data

[63] Continuation of Ser. No. 950,730, Oct. 12, 1978, abandoned.

[30] Foreign Application Priority Data

Jan. 20, 1978 [IT] Italy ............................... 19458 A/78

[51] Int. Cl.³ .............................................. C12Q 1/42
[52] U.S. Cl. ..................................... 435/21; 252/408; 424/7
[58] Field of Search .......................... 435/21, 805, 810; 424/2, 7; 252/408 R

[56] References Cited

U.S. PATENT DOCUMENTS

| | | | |
|---|---|---|---|
| 2,359,052 | 9/1944 | Scharer | 435/21 |
| 3,425,912 | 2/1969 | Deutsch et al. | 435/21 |
| 3,466,306 | 9/1969 | Babson | 435/21 |
| 4,132,598 | 1/1979 | Modrovich | 435/21 |

OTHER PUBLICATIONS

Ellis, "Quality Control of Serum Alkaline Phosphatase Assays. Project report and discussion of some factors affecting the assay", *Chem. Absts.*, vol. 84, No. 17, p. 180 (1976), Abs. No. 117450x.

McComb et al., "Study of Optimum Buffer Conditions for Measuring Alkaline Phosphatase Activity in Human Serum", *Clin. Chem.*, vol. 18, No. 2 (1972), pp. 97–104.

*Primary Examiner*—Thomas Wiseman
*Attorney, Agent, or Firm*—Morgan, Finnegan, Pine, Foley & Lee

[57] ABSTRACT

A novel composition is disclosed for determining the activity of the alkaline phosphatase, which comprises a salt of p-nitrophenylphosphoric acid, a magnesium salt, sodium borate and 2-amino-2-hydroxymethyl-1,3-propanediol. The composition affords advantages over the known composition especially as regards sensitivity.

5 Claims, 1 Drawing Figure

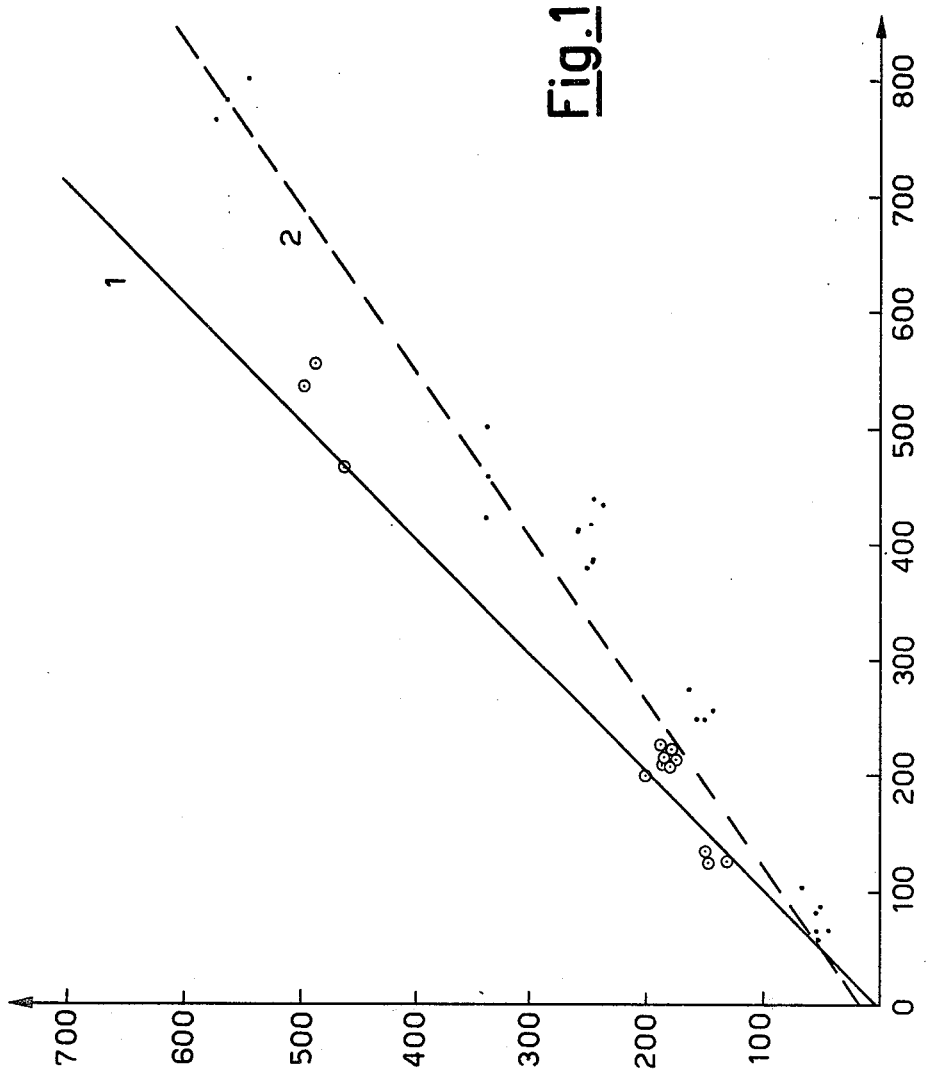

COMPOSITION FOR THE ANALYSIS OF THE ALKALINE PHOSPHATASE AND METHOD THEREFOR

This is a continuation of application Ser. No. 950,730 filed Oct. 12, 1978 now abandoned.

This invention relates to a novel composition which is adapted to the determination alkaline phosphatase, such composition being composed by a salt of para-nitrophenylphosphoric acid, a salt of magnesium, sodium borate and 2-amino-2-hydroxymethyl-1,3-propanediol. The invention also relates to a method for determining alkaline phosphatase, which method is based on the use of such a composition.

It is known that alkaline phosphatase is predominantly concentrated in the intestinal epithelium, in the portion of the bones which undergo growth, in the kidney cortex, in the mammary glands, in the liver, in the bile, in the blood and in the placenta as well. The action of the alkaline phosphatase is manifested in the catalysis of hydrolysis reaction of orthophosphates according to the reaction scheme:

$$R-O-PO(OH)_2 + H_2O \rightleftharpoons R-OH + H_3PO_4 \quad (1)$$

and its presence at high concentrations in the blood is evidence of a certain pathological condition of the human system: an increase of the phosphatase activity is an indication, for example, of disease of hepatic, intestinal or bone origin.

The first determination of the alkaline phosphatase in the human-blood-serum dates back to 1930 (Kay, H. D., J. Biol. Chem., 89, 235 (1930)), and since those early times, the methods of assay of the enzymic activity have undergone many changes, especially due to the influence thereon of the medium in which the reaction is caused to take place.

A number of the methods which are adopted for the determination of the phosphatase activity are now based (J. Biol., Chem., 172, 1 (1948)) on the discovery, by Axelrod, of the fact that the phosphatase enzyme is also capable of catalytically spurring the transphosphorylation reaction between the orthophosphate indicated in the reaction pattern (1) reported above, and an alcohol, which acts as a receptor.

An optical method is now being widely used for the determination of the activity of the alkaline phosphatase, such optical method providing for the use of p-nitrophenylphosphates as the first substrate for carrying out the transphosphorylation reaction mentioned above. The method provides for the admixing of the first substrate, to the second substrate (acceptor) and the enzyme, under the appropriate conditions, and the readout of the optical density at 400-415 nm, the readings being progressively taken during progress of the reaction. The increase of the optical density, as time goes by, is proportional to the quantity of the product which is being transformed so that an appropriate recordal of the data permits to deduce the activity of the enzyme.

Now, it is well known (see, for example, the book "The Enzymes", by Academic Press, 1961, pages 55 and ff), that alkaline phosphatase has an optimum activity in the vicinity of a pH of 10, and that its activity is improved by the presence of mineral salts, especially magnesium salts. These facts have compelled all the preparations which are commercially used for the determination of the phosphatase enzyme, to use ingredients which are both rigorously defined and legally required.

Thus, the use has become widespread of derivatives of p-nitrophenylphosphoric acid in combination with organic magnesium salts and buffers as required to maintain the above indicated pH range. The reagents that were initially used, were made a the sodium salts of the acid and inorganic buffers.

It has been ascertained that the sodium-nitrophenylphosphate has a poor stability and thus, in more recent times, it has been preferred to resort to the use of salts of the acid in question with amine compounds.

The preparation of p-nitrophenylphosphates, including those of amine compounds, and their use in biological formulations, are well known (see, for example, JACS, 79, (1957), page 3741.

Attempts have also been made with a view to improving the progress of the transphosphorylation reaction and, in the initial composition, the acceptor substances have been thus changed until arriving, lastly, at the use of buffers which simultaneously displayed the twofold action of keeping the pH value constant while concurrently acting as acceptors in the transphosphorylation reaction.

The care which must be taken when preparing the several buffers must not be overlooked, and such a care has, of course, its bearing on the overall economy of the reagent and the analysis. However, all the mixtures as used heretofore still suffer from a number of drawbacks, the most prominent of which is the poor stability of the reagent in time. Even if they are stored under drastic conditions, the prior art compositions cannot be used with reliability as to the reproducibility of the result, more than two or three days from their preparation, at the most.

In addition, many of the conventional reagents, such as those which use mannitol and like polyhydric alcohols as the acceptors in the transphosphorylation reaction, are capable of determining with a good sensitivity also the alkaline phosphatse of placental origin.

In the majority of the cases, determining the activity of the alkaline phosphatase is carried out in order to detect pathological conditions which can be attributed to the hepatic system (obstruction jaundice), the bone system (such as tumours, and Paget's disease), or the bowel system. Thus, in the case of pregnancy, the high physiological activity of the alkaline phosphatase in the blood may mask one or more of the pathological patterns mentioned above.

The Applicants have now surprisingly ascertained that a novel composition permits that the determination of the alkaline phosphatase may be carried out to give reproducible results without suffering from any of the shortcomings recalled hereinabove.

The composition concerned is composed by a salt of the p-nitrophenylphosphoric acid, a magnesium salt, sodium borate and 2-amino-2-hydroxymethyl-1,3-propanediol.

The composition is stable and retains for many days its initial properties, it is only slightly sensitive to the presence of phosphatases of placental origin. Moreover, it does not require an accurate preparation of a buffer, since the pH of the transphosphorylation reaction is provided by the ingredients of the composition themselves.

The method suggested herein provides, obviously, the reaction sequence

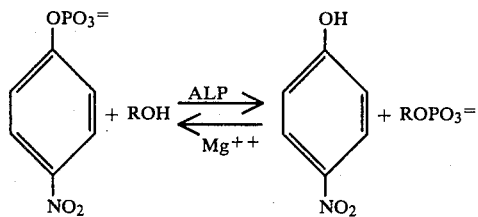

again, in which ALP is the alkaline phosphatase (EC 3.13.1.) and ROH is the propanediol mentioned above. Inasmuch as the reaction takes place at an alkaline pH value, the hydrolysis of the p-nitrophenylphosphate to p-nitrophenol is monitored by merely reading out the extinction at 405 nm.

As a matter of fact, under alkaline pH conditions, the p-nitrophenol is strongly colored in yellow whereas the p-nitrophenylphosphate is colorless.

The method permits to meter the alkaline phosphatase activity with a single mixture of reagents: it can be used manually, or also by applying it to automatic discrete and continuous-flow apparatuses. It can be used also for kinetic determinations and also for "fixed time" determinations by the addition of a blocking agent.

For performing the method many starting substrates can be used, even though, of course, it is preferred to avoid the use of the sodium salt of the p-nitrophenylphosphoric acid, on account of the tendency of the latter to become hydrolyzed spontaneously. Thus, there can be indicated as Examples the salts of the 2-amino-2-methyl-1,3-propanediol, of 2-amino-2-ethyl-1,3-propanediol, of 2-amino-2-hydroxymethyl-1,3-propanediol, of cyclohexylamine, just to cite a few of them.

The donor substrate, obviously, can be formulated as desired, since the affinity towards the enzyme is due to the p-nitrophenylphosphoric acid rather than to the salification agent.

Likewise, the magnesium salt can be selected from among a wide variety of compounds such as acetates, aspartates, chlorides, sulfates.

Good results have been obtained, for example, by employing the salt of cyclohexylamine of p-nitrophenylphosphoric acid as the donor substrate and the acetate of magnesium as the activator of the enzymic reaction.

As regards the 2-amino-2-hydroxymethyl-1,3-propanediol, that is the acceptor, its concentration in the conpositions contemplated herein must range from 0.7 molar to 2 molar.

EXAMPLE 1

The present Example relates to the preparation of 50 kilograms of reagent powder starting from the salts of the p-nitrophenylphosphoric acid (pNPP) with 2-amino-2-ethyl-1,3-propanediol (2A2E1, 3PD), with 2-amino-2-methyl-1,3-propanediol (2A2M1, 3PD) and with cyclohexylamine (CEA). The acceptor, that is, 2-amino-2-hydroxymethyl-1,3-propanediol has been called herein TRIS for short. There have been dried about 1.5 kg of pNPP-CEA.H2O under vacuum and over $P_2O_5$ at a temperature not exceeding 30° C., for about 48 hours in the dark. The final moisture contents must be 1.5% as a maximum.

As regards the pNPP-2A2E1, 3PD, or the pNPP-2A2M1, 3PD, the drying step was carried out only if the moisture contents of the product was over 0.5%.

The grit size of the several ingredients (TRIS), pNPP, Mg acetate, Na borate) was made uniform by grinding and/or screening.

There were mixed subsequently 48.35 kilograms of TRIS with 68.6 grams of Mg acetate.4H2O and with 683.5 grams of Na tetraborate.10H2O until homogeneization of the powders was achieved.

The powder was placed on stainless steel trays, plates or other suitable supporting vessels and dried at 70° C. for about 14 hours.

The whole was cooled in an anhydrous environment and screened again to make the grit size of the mixture uniform. The final moisture contents had to be less than 0.6%.

There have been obtained 48.76 kilograms of base powder. The base powder was combined with 1.37 kilograms of pNPP-CAE (or with 1.49 kilograms of pNPP-2A2E1, 3PD, or with 1.40 kilograms of pNPP-2A2M1, 3PD) and the entire lot was thoroughly blended.

A statistical check for ascertaining the homogeneity of the mixture has been carried out by sampling random scantlings (3.5 grams of mixture plus 20 mls H2O) and determining thereon the pH, the magnesium and the pNPP.

The final moisture contents was not over 0.8%.
Distribution.

By using the different pNPP, there have been obtained, respectively,

| | |
|---|---|
| 50.13 kilograms when using pNPP-CEA | I |
| 50.25 kilograms when using pNPP-2A2E, 3PD | II |
| 50.16 kilograms when using pNPP-2A2M1, 3PD | III |

To the end of the practical use of the reagent, the following considerations have been made. An individual ALP test (3 mls) corresponds to 483 milligrams of I or of III and to 484 milligrams of II.

Since, by dissolving the powder in a certain volume of H2O, the volume is increased by about 12.5%, it is possible to calculate the weight of powder to be distributed in the flask, to which there must be added 20 mls of H2O, 22.5 mls being obtained as the dissolution is completed.

483 by 22.5:3 = 3622 milligrams per flask of I or of III
484 by 22.5:3 = 3630 milligrams per flask of II In the two-liter flasks of complete solution, there must be distributed, conversely:
322 grams of I or of III, and
323 grams of II, respectively.

EXAMPLE 2

One of the reagents as prepared according to the previous Example has been employed for determining the alkaline phosphatase activity.

The reagent has been heated previously to the reaction temperature and then a 3-ml scantling has been admixed with 0.05 mls of the sample to be tested. The whole has been placed in a photometric readout apparatus at 405 mm at the preselected constant temperature.

The variation of the optical density ($\Delta O.D.min^{-1}$) has been measured. For $\Delta O.D.min^{-1}$ higher than 0.750 (equivalent to about 2,500 mU/ml) the measurement was repeated on a sample diluted to 1:10. In this case the result had to be multiplied by 10.

The $\Delta O.D.\min^{-1}$ which had been found was introduced in the following calculation, to obtain the mU/ml:

$$\Delta O.D.\min^{-1} \text{ by } \frac{1000 \cdot V_t}{18.6 \cdot L_p \cdot V_s} = \text{mU/ml}$$

wherein:
1000 is the factor to pass from units to thousandths of units.
$V_t$ is the total reaction volume, i.e. 3.05 mls
18.6 is the millimolar extinction coefficient of pNP
$L_p$ is the light path which is 1 cm
$V_s$ is the volume of the sample being tested, which is 0.05 ml
Now, therefore:
mU/ml = $\Delta O.D.\min^{-1}$ multiplied by 3280

EXAMPLE 3

Comparison tests have been carried out between the composition hereof and a conventional composition for the determination of the alkaline phosphatase, the conventional composition being made up by the salt of pNPP with CEA, magnesium aspartate and a carbonate buffer. There have been used the same quantities as specified in the previous Example at a temperature of 37° C.

The results are plotted in the graph of FIG. 1 wherein the abscissae indicate the mU/ml which have been obtained when using the composition according to this invention, whereas the ordinates indicate the mU/ml which have been obtained by using the conventional composition.

The straight line 1 is the ideal curve which would be obtained if both compositions should give the same results. The marking ⊙ (circled dots) are referred to samples of phosphatase of placental origin. The straight line 2 is referred to the actual linear regression curve of the conventional composition relative to the composition of the invention. Such a regression is evidence of the fact that the method disclosed herein is more sensitive than the conventional one and is such by more than 20% (see the angular deviation relative to the ideal curve).

Such an improved sensitivity is not experienced for the phosphatases of placental origin: in the case of this invention, thus, the placental phosphatase is undetermined relative to the conventional methods. The uncircled dots, in fact, refer to samples which contain phosphatase of different origins, such as hepatic, bony, intestinal. The curve 2 reproduces the equation $Y = 0.727x + 9.01$, the curve 1 being obviously the reproduction with $Y = x$.

I claim:
1. A composition for the analysis of alkaline phosphatase, said composition consisting essentially of a salt of p-nitro-phenylphosphoric acid, a magnesium salt, sodium borate and 2-amino-2-hydroxymethyl-1,3-propanediol.
2. A composition for the determination of alkaline phosphatase according to claim 1, wherein the 2-amino-2-hydroxymethyl-1,3-propanediol is present at a concentration between 0.7 molar to 2-molar
3. A composition for the analysis of alkaline phosphatase according to claim 1 wherein the salt of the p-nitrophenylphosphoric acid is selected from among the salts of 2-amino-2-methyl-1,3-propanediol, and cyclohexylamine.
4. A composition for the analysis of alkaline phosphatase according to claim 1 wherein the magnesium salt is selected from among magnesium acetate, aspartate, chloride and sulfate.
5. A method for the determination of non-placental alkaline phosphatase which comprises contacting a sample containing both placental and non-placental alkaline phosphatase to be tested with a composition consisting essentially of a salt of p-nitrophenylphosphoric acid, a salt of magnesium, sodium borate and 2-amino-2-hydroxymethyl-1,3-propanediol and thereafter photometrically determining the amount of non-placental alkaline phosphatase.

* * * * *